United States Patent [19]

Mano et al.

[11] Patent Number: 6,037,355

[45] Date of Patent: Mar. 14, 2000

[54] IMIDAZOLE LIPOXYGENASE INHIBITORS

[75] Inventors: Takashi Mano; Rodney W. Stevens, both of Handa, Japan

[73] Assignee: Pfizer Inc, New York, N.Y.

[21] Appl. No.: 09/043,256

[22] PCT Filed: Jul. 24, 1996

[86] PCT No.: PCT/IB96/00744

§ 371 Date: Jun. 29, 1998

§ 102(e) Date: Jun. 29, 1998

[87] PCT Pub. No.: WO97/11079

PCT Pub. Date: Mar. 27, 1997

[30] Foreign Application Priority Data

Sep. 18, 1995 [WO] WIPO ............... PCT/IB95/00767

[51] Int. Cl.[7] ............... A01N 43/40; A01N 43/50; C07D 401/04; C07D 233/02

[52] U.S. Cl. ............... 514/341; 514/399; 546/274.1; 548/311.1; 548/315.4

[58] Field of Search ............... 514/341, 399; 546/274.1; 548/311.1, 315.4

[56] References Cited

U.S. PATENT DOCUMENTS 5,753,682  5/1998  Stevens et al. ............... 514/341

FOREIGN PATENT DOCUMENTS

| 0462812 | 12/1991 | European Pat. Off. . |
| 0462830 | 12/1991 | European Pat. Off. . |
| 9427999 | 12/1994 | WIPO . |
| 9429299 | 12/1994 | WIPO . |
| 9503309 | 2/1995 | WIPO . |

Primary Examiner—Mukund J. Shah
Assistant Examiner—Tamthom N. Truong
Attorney, Agent, or Firm—Peter C. Richardson; Paul H. Ginsburg; Seth H. Jacobs

[57] ABSTRACT

The present invention provides a compound of formula (I):

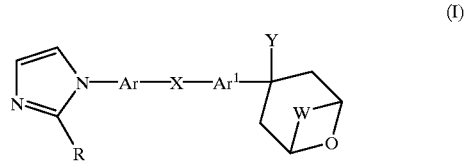

and a pharmaceutically acceptable salt thereof, wherein Ar is phenylene optionally substituted with halo, hydroxy, cyano, $C_1$–$C_4$ alkyl, $C_1$–$C_4$ alkoxy, $C_1$–$C_4$ alkylthio, $C_1$–$C_4$ halo-substituted alkyl or $C_1$–$C_4$ halo-substituted alkoxy, X is —A—$X^1$— or —$X^2$—A—, where A is a direct bond or $C_1$–$C_4$ alkylene, and $X^1$ is oxy, thio, sulfinyl or sulfonyl; Ar is phenylene, pyridylene or thienylene optionally substituted with halo, hydroxy, cyano, nitro, amino, $C_1$–$C_4$ alkyl, $C_1$–$C_4$ alkoxy, $C_1$–$C_4$ alkylthio, $C_1$–$C_4$ halo-substituted alkyl, $C_1$–$C_4$ halo-substituted alkoxy, $C_1$–$C_4$ alkylamino or di($C_1$–$C_4$)alkylamino; Y is CN or $CONR^1R^2$ wherein $R^1$ and $R^2$ are independently hydrogen or $C_1$–$C_4$ alkyl; and R is hydrogen or $C_1$–$C_6$ alkyl; W is $C_2$–$C_3$ alkylene, one carbon atom of which may be replaced by an oxygen atom. Further the invention provides a pharmaceutical composition for treating an inflammatory disease, allergy or cardiovascular diseases or the like in a mammalian subject which comprises a compound of formula (I) and a pharmaceutically acceptable carrier.

11 Claims, No Drawings

IMIDAZOLE LIPOXYGENASE INHIBITORS

This is a 371 application of PCT/IB 96/0074 filed on Jul. 24, 1996.

TECHNICAL FIELD

This invention relates to novel imidazole lipoxygenase inhibitors. The compounds of the present invention inhibit the biosynthesis of leukotrienes by intervention of the action of the enzyme 5-lipoxygenase on arachidonic acid and are therefore useful in the treatment or alleviation of inflammatory diseases, allergy and cardiovascular diseases in mammals. This invention also relates to pharmaceutical compositions comprising such compounds.

BACKGROUND ART

Arachidonic acid is known to be the biological precursor of several groups of biologically active endogenous metabolites. The first step in the metabolism of arachidonic acid is its release from membrane phospholipids, via the action of phospholipase $A_2$. Arachidonic acid is then metabolized either by cyclooxygenase to produce prostaglandins including prostacyclin, and thromboxanes or by lipoxygenase to generate hydroperoxy fatty acids which may be further converted to the leukotrienes.

The leukotrienes are extremely potent substances which elicit a wide variety of biological effects, often in the nanomolar to picomolar concentration range. The peptido-leukotrienes ($LTC_4$, $LTD_4$, $LTE_4$) are important bronchoconstrictors and vaso-constrictors, and also cause plasma extravasation by increasing capillary permeability. $LTB_4$ is a potent chemotactic agent, enhancing the influx of leukocytes and inducing their subsequent degranulation at the site of inflammation. A pathophysiological role for leukotrienes has been implicated in a number of human disease states including asthma and related obstructive airway diseases, allergic rhinitis, rheumatoid arthritis and gout, psoriasis and atopic dermatitis, adult respiratory distress syndrome (ARDS), inflammatory bowel diseases (e.g. Crohn's disease), endotoxin shock, atherosclerosis and cardiovascular disorders (e.g. ischemia-induced myocardial injury) and glomerular nephritis. Any agent that inhibits the action of 5-lipoxygenase is expected to be of considerable therapeutic value for the treatment of acute and chronic inflammatory conditions.

For a review article on lipoxygenase inhibitors, see H. Masamune and L. S. Melvin, Sr.: Annual Reports in Medicinal Chemistry, 1989, 24, pp 71–80 (Academic). More recently, further examples of lipoxygenase inhibitors have been disclosed in WO 95/03309 and WO94/29299.

BRIEF DISCLOSURE OF THE INVENTION

The present invention provides a novel chemical compound of formula I:

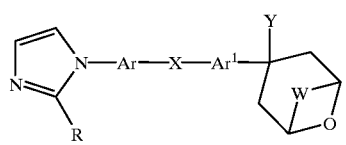

I and a pharmaceutically acceptable salt, wherein
Ar is phenylene optionally substituted with halo, hydroxy, cyano, amino, $C_1$–$C_4$ alkyl, $C_1$–$C_4$ alkoxy, $C_1$–$C_4$ alkylthio, $C_1$–$C_4$ halo-substituted alkyl, $C_1$–$C_4$ halo-substituted alkoxy;

X is —A—$X^1$— or —$X^1$A—, wherin A is a direct bond or $C_1$–$C_4$ alkylene, and $X^1$ is oxy, thio, sulfinyl or sulfonyl;

$Ar^1$ is phenylene, pyridylene or thienylene optionally substituted with halo, hydroxy, cyano, nitro, amino, $C_1$–$C_4$ alkyl, $C_1$–$C_4$ alkoxy, $C_1$–$C_4$ alkylthio, $C_1$–$C_4$ halo-substituted alkyl, $C_1$–$C_4$ halo-substituted alkoxy, $C_1$–$C_4$ alkylamino, di($C_1$–$C_4$)alkylamino;

Y is CN or $CONR^1R^2$ wherein $R^1$ and $R^2$ are independently hydrogen or $C_1$–$C_4$ alkyl; and R is hydrogen or $C_1$–$C_6$ alkyl; and W is $C_2$–$C_3$ alkylene, one carbon atom of which may be replaced by an oxygen atom.

A preferred group of compounds of this invention includes compounds of the formula I, wherein Ar is phenylene optionally substituted with halo or $C_1$–$C_4$ alkyl; X is oxy or thio; $Ar^1$ is phenylene optionally substituted with halo or $C_1$–$C_4$ alkyl; Y is CN or $CONR^1R^2$ wherein $R^1$ and $R^2$ are independently hydrogen or $C_1$–$C_2$ alkyl; R is $C_1$–$C_3$ alkyl; and W is $C_2$–$C_3$ alkylene.

A more preferred group of compounds of this invention includes compounds of the formula I, wherein Ar is 1,4-phenylene optionally substituted with halo or $C_1$–$C_4$ alkyl, more preferably 1,4-phenylene; X is thio; $Ar_1$ is 1,3-phenylene optionally substituted with halo or $C_1$–$C_4$ alkyl, more preferably 1,3-phenylene; Y is CN or $CONH_2$; R is $C_1$–$C_2$ alkyl, more preferably methyl; and W is $C_2$–$C_3$ alkylene, more preferably ethylene.

Preferred individual compounds of this invention include:
endo-3-Cyano-exo-3-[3-[4-(2-methylimidazol-1-yl)phenyl]thiophenyl]- 8-oxabicyclo[3.2.1]octane or its salts; and
exo-3-Cyano-endo-3-[3-[4-(2-methylimidazol-1-yl)phenyl]thiophenyl]-8-oxabicyclo[3.2.1]octane or its salts.

Preferred individual compounds of this invention also include:
endo-3-Aminocarbonyl-exo-3-[3-[4-(2-methylimidazol-1-yl)phenyl]thiophenyl]-8-oxabicyclo[3.2.1]octane or its salts; and
exo-3-Aminocarbonyl-endo-3-[3-[4-(2-methylimidazol-1-yl)phenyl]thiophenyl]-8-oxabicyclo[3.2.1]octane or its salts.

This invention provides a pharmaceutical composition for the treatment of an allergic or inflammatory condition in a mammalian subject which comprises a therapeutically effective amount of a compound of formula I and a pharmaceutically acceptable carrier.

This invention also provides a method for treatment of a medical condition for which a 5-lipoxygenase inhibitor is needed, in a mammalian subject, which comprises administering to said subject a therapeutically effective amount of a compound of formula I. Preferrably, the medical condition is an allergic or inflammatory condition.

These compounds are useful in the treatment or alleviation of inflammatory diseases, allergy and cardiovascular diseases, etc. in mammals and as the active ingredient in pharmaceutical compositions for treating such conditions.

DETAILED DESCRIPTION OF THE INVENTION

In this application, the following terms are used.

The term "exo" means that position in a bicyclic molecule nearer the main bridge, and the term "endo" means that position in a bicyclic molecule opposite the main bridge. The main bridge is determined by applying the priorities (highest first): (1) bridge with hetero atoms; (2) bridge with fewest members; (3) saturated bridge; (4) bridge with fewest substituents; (5) bridge with lowest priority substituents.

General Synthesis

A compound of formula I may be prepared by any synthetic procedure applicable to structurally-related compounds known to those skilled in the art. The following representative examples are illustrative of the invention in which, unless otherwise stated, Ar, $X^1$, $Ar^1$, Y, A, R and W are as defined herein before. For example, the compound of the formula I may be prepared according to the reaction outlined in Scheme 1.

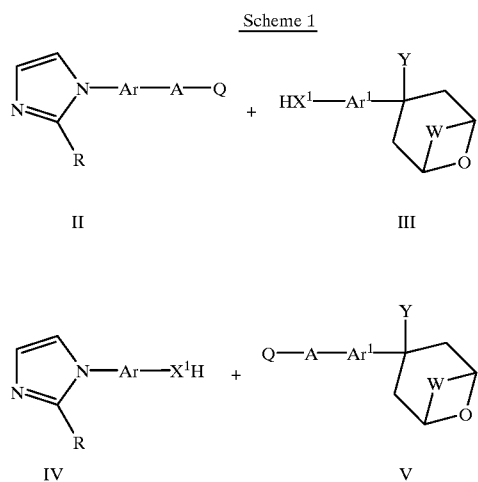

In one embodiment, a compound of formula II (or formula V) wherein Q is a displaceable group is coupled with a compound of formula III (or formula IV), preferably in the presence of a suitable base. A suitable displaceable group Q is, for example, a halo or sulfonyloxy group, for example, fluoro, chloro, bromo, iodo, trifluoromethanesulfonyloxy, methanesulfonyloxy or p-toluenesulfonyloxy group, all readily accessible by conventional methods. Preferred base for the coupling reaction is, for example, an alkali or alkaline earth metal hydroxide, alkoxide, carbonate or hydride such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, diisopropylethylamine or dimethylaminopyridine. Preferred reaction-inert solvents include, for example, acetone, acetonitrile, dichloromethane, N,N-dimethylacetamide, N,N-dimethylformamide, dimethylsulfoxide, dioxane or tetrahydrofuran. Reaction temperatures are preferably in the range of –40° C. to 200° C., usually in the range of room temperature to reflux temperature of solvent, but if necessary, lower or higher temperature can be employed. Reaction time is in general from 30 minutes to 10 days, preferably from 2 hours to 5 days. Conveniently the reaction may be conducted in the presence of a suitable catalyst, for example, tetrakis(triphenylphosphine)—palladium, bis (triphenylphosphine)palladium(II) chloride, cuprous oxide, cuprous iodide, cuprous bromide or cuprous chloride.

Alternatively, a compound of formula II (or formula V) wherein Q is a hydroxyl group and A is $C_1$–$C_4$ alkylene, for example methylene, is coupled with a compound of formula III (or formula IV) under Mitsunobu-type reaction conditions. Suitable condensing reagents are, for example, diethyl azodicarboxylate and triphenylphosphine and preferred reaction-inert solvents include dichloromethane, tetrahydrofuran and toluene. Reaction temperatures are preferably in the range of 0° C. through to 60° C., usually to room temperature, but if necessary, lower or higher temperature can be employed. Reaction time is in general from 30 seconds to 1 day, preferably from 2 minutes to 5 hours.

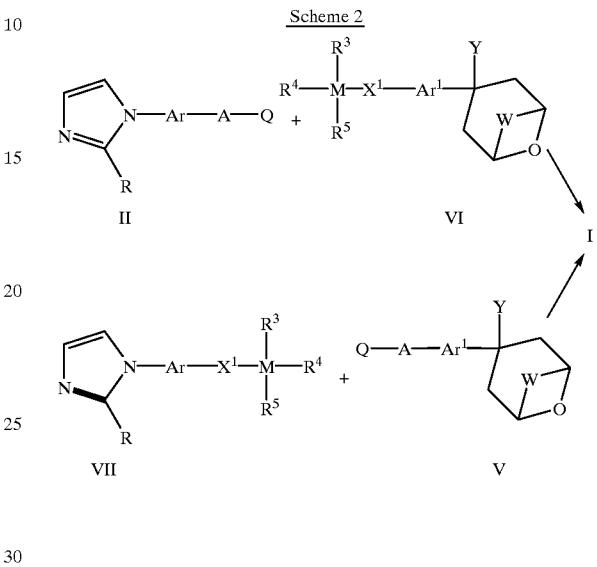

In another embodiment (Scheme 2), a compound of formula II (or formula V) wherein Q is a displaceable group is coupled with a compound of formula VI (or formula VII) wherein $R^3$, $R^4$ and $R^5$ are independently a suitable alkyl group such as $C_1$–$C_4$ alkyl or aryl such as a phenyl or optionally substituted phenyl group and M is silicon or tin (IV), preferably silicon, preferably in the presence of a suitable base. A suitable displaceable group Q is, for example, a halo or sulfonyloxy group, for example, fluoro, chloro, bromo, iodo, trifluoromethanesulfonyloxy, methanesulfonyloxy or p-toluenesulfonyloxy group, all readily accessible by conventional methods. A suitable —$MR^3R^4R^5$ group is, for example, trimethylsilyl, triisopropylsilyl, tert-butyldimethylsilyl or tert-butyldiphenylsilyl, preferably triisopropylsilyl, or tributylstannyl, all readily accessible by conventional methods. Preferred base for the coupling reaction is, for example, an alkali or alkaline earth metal alkoxide, or halide such as sodium ethoxide, sodium tert-butoxide, potassium tert-butoxide, sodium fluoride, potassium fluoride, or cesium fluoride, or a quartenary ammonium salt such as tetrabutylammonium fluoride. Preferred reaction-inert solvents include, for example, ethanol, acetonitrile, toluene, N,N-dimethylacetamide, N-methyl-2-pyrrolidone, N,N-dimethylformamide, dimethylsulfoxide, dioxane or tetrahydrofuran. Reaction temperatures are preferably in the range of –40° C. to 200° C., usually in the range of room temperature to reflux temperature of solvent, but if necessary, lower or higher temperature can be employed. Reaction time is in general from 30 minutes to 10 days, preferably from 2 hours to 5 days. Conveniently the reaction may be conducted in the presence of a suitable catalyst, for example, tetrakis(triphenylphosphine)palladium, bis (triphenylphosphine)palladium (II) chloride, or the like (for example, see Tetrahedron Lett., 1994, 3225–3226).

Scheme 3

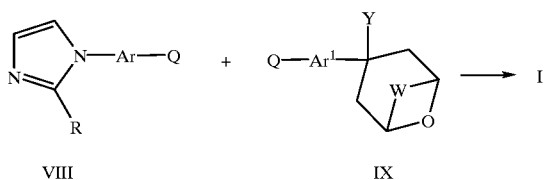

VIII    IX

Alternatively, in another embodiment, a compound of formula VIII is coupled with a compound of formula IX, wherein Q is a displaceable group, in the presence of thiourea and a suitable catalyst, for example, tetrakis (triphenylphosphine)palladium, or a nickel(0) catalyst generated in situ from, for example, bis(triethylphospliine)nickel(II) chloride and a suitable reducing agent such as, for example, sodium cyanoborohydride, or the like (for example, see Chem. Lett., 1986, 1379–3226). A suitable displaceable group Q is, for example, a halo or sulfonyloxy group, for example, fluoro, chloro, bromo, iodo, trifluoromethanesulfonyloxy, methanesulfonyloxy or p-toluenesulfonyloxy group, all readily accessible by conventional methods. Preferred reaction-inert solvents include, for example, ethanol, acetonitrile, toluene, N,N-dimethylacetamide, N-methyl-2-pyrrolidone, N,N-dimethylformamide, dimethylsulfoxide, dioxane or tetrahydrofuran. Reaction temperatures are preferably in the range of −40° C. to 200° C., usually in the range of room temperature to reflux temperature of solvent, but if necessary, lower or higher temperature can be employed. Reaction time is in general from 30 minutes to 10 days, preferably from 2 hours to 5 days.

For the preparation of those compounds in Formula I wherein $X^1$ is sulfinyl or sulfonyl group, a compound of formula I wherein $X^1$ is thio may be oxidized by conventional methods. A suitable oxidizing agent is, for example, hydrogen peroxide, a peracid such as m-chloroperoxybenzoic or peroxyacetic acid, an alkaline metal peroxysulfate such as potassium peroxymonosulfate or the like. Preferred reaction-inert solvents include, for example, acetone, dichloromethane, chloroform, tetrahydrofuran, methanol or water. Reaction temperatures are preferably in the range 0° C. to room temperature, but if necessary, lower or higher temperature can be employed. Reaction time is in general from a few minutes to several hours.

The starting materials of the formulae II, III, IV, V, VI, VII, VIII and IX may be conveniently obtained by conventional procedures known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples herein may be isolated by standard methods and purification can be achieved by conventional means known to those skilled in the art, such as distillation, recrystallization and chromatography techniques.

The compounds of the present invention which contain one or more asymmetric centers are capable of existing in various stereoisomeric forms. All such individual forms, and mixtures thereof, are included within the scope of the invention. The various isomers can be obtained by standard methods. For example, racemic mixtures can be separated into the individual enantiomers by standard resolution techniques. Individual diastereomers can be obtained by stereoselective synthesis, or by separation of mixtures by fractional crystallization or chromatography techniques.

A majority of the compounds of the present invention are capable of forming addition salts with inorganic and organic acids. The pharmaceutically acceptable acid salts of the novel compounds of the present invention are readily prepared by contacting said compound with a chosen mineral or organic acid in an aqueous solvent medium, in a suitable organic solvent, such as, for example, methanol, ethanol, acetone or diethyl ether, or mixture thereof. The desired solid salt may then be obtained by precipitation or by careful evaporation of solvent.

The acids which are used to prepare the pharmaceutically acceptable acid addition salts of the aforementioned compounds of the present invention are those which form non-toxic addition salts, such as the hydrochloride, hydrobromide, hydroiodide, nitrate, sulfate or acetate, fumarate, tartrate, succinate, maleate, gluconate, saccharate, benzoate, methanesulfonate, benzenesulfonate, p-toluenesulfonate and pamoate (i.e., 1,1'-methylene-bis-(2-hydroxy-3-naphthoate)) salts.

The compounds of the invention which have also acidic groups are capable of forming base salts with various pharmaceutically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form non-toxic base salts. These particular non-toxic base salts include those derived from such pharmaceutically acceptable cations as sodium, potassium, calcium and magnesium, etc. These salts can easily be prepared by treating the aforementioned compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The compounds of the present invention inhibit the activity of 5-lipoxygenase enzyme. This inhibition was demonstrated in vitro using heparinised human whole blood and in vivo using a platelet-activating factor-induced lethality assay in mice as described in detail hereinafter.

In Vitro Assay Using Heparinized Human Whole Blood (HWB)

Inhibition has been demonstrated in vitro using heparinised human whole blood (*British Journal of Phannacology*: 1990 99, 113–118), which determines the inhibitory effect of said compounds on 5-lipoxygenase (LO) metabolism of arachidonic acid. Aliquots of heparinized human whole blood (1 ml) from healthy donors were preincubated with drugs dissolved in dimethyl sulfoxide (final concentration, 0.1%) for 10 min at 37° C., then calcium ionophore A21387 (60 μM) and Heparapid (2.5%, Sekisui Chemical Co. LTD., Japan) were added and incubations were continued for further 30 min. Reactions were terminated by rapid cooling in an ice bath. Blood-clots induced by Heparapid were removed by centrifugation. Acetonitrile (ACN, 1.5 ml) and PGB$_2$ (500 ng, as internal standard) were added to supernatants. Samples were mixed by Voltex mixer and precipitated proteins were removed by centrifugation. Supernatants were diluted 7ml of water and were loaded onto a prewashed Sep-Pak C$_{18}$ cartridge (Waters Associates, Milford, MS, USA) and arachidonate metabolites were eluted with 4 ml of 70% methanol. Methanolic extract was evaporated and the residue was then reconstituted in 100 µl of 50% aqueous ethanol.

Reconstituents (40 µl) were injected onto a reversed phase C$_{18}$ column (Wakosil 5C18, 4.6×150 mm, Wako Pure Chemical Industries LTD, Japan). Column temperature was 40° C. HPLC analysis was performed by Hewlett Packard model 1090M HPLC system. The chromatographic was achieved by gradient elution using two different mobile phase (mobile phase A consisted of 10% ACN, 0.1% trifluoroacetic acid and 0.05% triethylamine; mobile phase B consisted of 80% ACN, 0.1% trifluoroacetic acid and 0.05% triethylamine). Each mobile phase was continuously sparged with helium. The HPLC gradient was programmed as follows (where A+B=100): from 0 to 9.7 min, a linear gradient from 35 to 100% of mobile phase A with flow rate of 1 ml/min. Peaks of eluting products were quantitated by UV absorbance (LTB$_4$ and PGB$_2$ at 275 nm; HHT and 5-HETE at 235 rm, respectively) and were corrected by PGB$_2$ recovery. Sigmoid regression was used to estimate IC$_{50}$ values.

In Vivo Platelet Activating Factor (PAF) Lethality Assay

The in vivo potency after oral administration of compounds to ICR mice (male) was determined using PAF lethality assay in a similar manner as described by J. M. Young et al. (J. M. Young, P. J. Maloney, S. N. Jubb, and J. S. Clark, *Prostaglandins*, 30, 545 (1985). M. Criscuoli and A. Subissi, *Br. J. Pharmac.*, 90, 203(1987). H. Tsunoda, S. Abe, Y. Sakuma, S. Katayama, and K. Katayama, *Prostaglandins Leukotiienes and Essential Fatty Acids*, 39, 291 (1990)). PAF was dissolved at a concentration of 1.2 mg/ml in 0.05 mg/ml propranolol-saline containing 0.25% BSA and injected intravenously into mice at a dose of 12 mg/Kg. Mortality was determined 1hr after PAF injection. To investigate the effect of LO inhibitors, compounds were dissolved in 5% Tween 80, 5% EtOH-saline and administered orally (0.1 ml/10 g) 45 min prior to PAF injection.

The compounds of the present invention tested in the aforementioned assays were shown to possess the ability to inhibit 5-lipoxygenase activity.

The ability of the compounds of the present invention to inhibit lipoxygenase enzyme makes them useful for controlling the symptoms induced by the endogenous metabolites arising from arachidonic acid in a mammalian subject, especially a human subject. The compounds are therefore valuable in the prevention and treatment of such disease states in which the accumulation of arachidonic acid metabolites are the causative factor; e.g. allergic bronchial asthma, skin disorders, rheumatoid arthritis and osteoarthritis.

In particular, the compounds of the present invention and their pharmaceutically acceptable salts are of use in the treatment or alleviation of inflammatory diseases in a human subject.

For treatment of the various conditions described above, the compounds and their pharmaceutically acceptable salts can be administered to a human subject either alone, or preferably in combination with pharmaceutically acceptable carriers or diluents in a pharmaceutical composition according to standard pharmaceutical practice. The compounds can be administered orally or parenterally in conventional fashion. When the compounds are administered to a human subject for the prevention or treatment of an inflammatory disease, the oral dose range will be from about 0.1 to 10 mg/kg per body weight of the subject to be treated per day, preferably from about 0.1 to 4 mg/kg per day in single or divided doses. If parenteral administration is desired, then an effective dose will be from about 0.05 to 5 mg/kg per body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

In general, the compounds of this invention are present in the above dosage forms at concentration level ranging 5% to 90% by weight, preferably 10% to 50 % by weight.

In addition, particularly for the treatment of asthma, the compounds of formula I of this invention can be administered to a human subject by inhalation. For this purpose they are administered as a spray or mist, according to standard practice.

EXAMPLES

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows:
s—singlet, d—doublet, t—triplet, m—multiplet and br—broad.

Example 1 endo-3-Cyano-exo-3-[3-[4-(2-methylimidazol-1-yl) phenyl]thiophenyl]-8-oxabicyclor[3.2.1]octane)

A. cis-2,5-Bis(iodomethyl)tetrahydrofuran

A mixture of cis-2,5-bis(tosyloxymethyl)tetrahydrofuran (Cope, A C.; Baxter, W. N. J. Am Chem. Soc. 1955, 77, 393) (2.78 g, 6.3 mmol) and sodium iodide (8.99 g, 60 mmol) in acetone (60 ml) was stirred under nitrogen at reflux for 2.5 days. Solids were filtered off and the filtrate was diluted with water (200 ml) and extracted with diethyl ether (200 ml). The ethereal extract was washed with brine (200 ml), dried (MgSO$_4$) and concentrated to dryness to give 2.12 g of a black liquid. Purification by silica gel column chromatography (15% ethyl acetate in n-hexane) afforded 1.87 g (84%) of the titled compound as a colorless liquid.

¹H-NMR (CDCl₃) δ: 4.15–4.04 (2 H, m), 3.29 (2 H, d, J=4.8, 9.9 Hz), 3.22 (2 H, dd, J=7.0, 9.9 Hz), 2.20–2.08 (2 H, m), 1.89–1.75 (2 H, m)

B. endo-3-Cyano-exo-3-(3-iodophenyl)-8-oxabicyclo[3.2.1]octane (1), and exo-3-Cyano-endo-3-(3-iodophenyl)-8-oxabicyclo[3.2.1]octane (2)

To a solution of 3-iodophenylacetonitrile (0.92 g, 3.8 mmol) in DMSO (20 ml) was added sodium hydride (60 % w/w dispersion in mineral oil, 0.36 g, 9.1 mmol). The reaction mixture was stirred for 15 min at room temperature and then a solution of cis-2,5-bis(iodomethyl)tetrahydrofuran (1.33 g, 3.8 mmol) in DMSO (20 ml) was added rapidly and stirring continued overnight. The reaction mixture was diluted with a mixture of water (100 ml) and brine (100 ml) and extracted with ethyl acetate (100 ml×3). The combined extracts were washed with a mixture of water (50 ml) and brine (50 ml) and then with brine (100 ml), dried (MgSO₄) and concentrated to dryness. Purification by silica gel column chromatography (ethyl acetate in n-hexane, increasing the ratio of ethyl acetate from 15 % to 25 %) gave 0.56 g (43 %) of the less polar bicyclic compound, endo-3-cyano-exo-3-(3-iodophenyl)-8-oxabicyclo[3.2.1]octane (1) as off-white solids and 0.22 g (17 %) of the more polar bicyclic compound, exo-3-cyano-endo-3-(3-iodophenyl)-8-oxabicyclo[3.2.1]octane (2) as white solids.

¹H-NMR
endo-3-Cyano-exo-3-(3-iodophenyl)-8-oxabicyclo[3.2.1]octane (1)

(CDCl₃) δ: 7.83 (1 H, dd, J=1.8, 1.8 Hz), 7.68–7.64 (1 H, m), 7.51–7.47 (1 H, m), 7.13 (1 H, dd, J=7.7, 8.1 Hz), 4.61–4.53 (2 H, m), 2.55–2.45 (2 H, m), 2.30 (2 H, dd, J=4.0, 14.3 Hz), 2.22 (2 H, dd, J=1.1, 14.3 Hz), 2.17–2.10 (2 H, m)

exo-3-Cyano-endo-3-(3-iodophenyl)-8-oxabicyclo[3.2.1]octane (2)

(CDCl₃) δ: 7.85 (1 H, dd, J=1.8, 1.8 Hz), 7.68 (1 H, dd, J=1.8, 8.1 Hz), 7.52 (1 H, dd, J=1.8, 8.1 Hz), 7.14 (1 H, dd, J=8.1, 8.1 Hz), 4.52–4.50 (2 H, m), 2.75 (2 H, dd, J=6.6, 14.7 Hz), 2.13 (2 H, dd, J=1.8, 14.7 Hz), 2.00–1.80 (2 H, m), 1.52–1.50 (2 H, m)

C. endo-3-Cyano-exo-3-[3-[4-(2-methylimidazol-1-yl)phenyl]thiophenyl]-8-oxabicyclo [3.2.1]octane A 30 ml two-necked flask was equipped with a stopper, a nitrogen inlet and a magnetic stirring bar. The flask was charged with sodium cyanoborohydride (5 mg, 0.08 mmol) and flushed with nitrogen (this process was repeated twice). Bis(triethylphosphine)nickel(II) chloride (Jensen, K A. Z. Anorg. Allg. Chem., 1936, 229, 265: Jensen, K. A.; Nielsen, P. H.; Pedersen, C. T. Acta Chem. Scand., 1963, 17, 1115) (14.6 mg, 0.04 mmol), endo-3-cyano-exo-3-(3-iodophenyl)-8-oxabicyclo[3.2.1]octane (339 mg, 1 mmol) and thiourea (114 mg, 1.5 mmol) were then added. N,N-Dimethylformamide (DMF, 1 ml) was added and the resulting mixture was heated at 60 ° C. under nitrogen for 4 h. After cooling to room temperature, calcium oxide (84 mg, 1.5 mmol) and DMF (1 ml) were added. The resulting mixture was stirred at room temperature under nitrogen for 1.5 h and then a mixture of 4-(2-methylimidazol-1-yl)phenyl iodide (284 mg, 1 mmol), bis(triethylphosphine)nickel(II) chloride (82 mg, 0.2 mmol) and sodium cyanoborohydride (25 mg, 0.4 mmol) was added. The resulting red mixture was heated at 60 ° C. under nitrogen for 4 h and then cooled to room temperature. The resulting deep red mixture was diluted with ethyl acetate (25 ml) and washed with a mixture of water (12.5 ml) and brine (12.5 ml) twice. The aqueous layers were extracted with another portion of ethyl acetate (25 ml). The combined organic layers were washed with brine (25 ml), dried (MgSO₄) and concentrated under reduced pressure to give 483 mg of a black liquid. The residue was purified by column chromatography using Lobar® pre-packed column size B (310–25) LiChroprep® NH₂ (40–63 μm) (Merck) eluting with ethyl acetate to afford 191 mg (48 %) of the titled compound as a colorless oil.

¹H-NMR (CCDl₃) δ: 7.61–7.57 (1 H, m), 7.50–7.31 (5 H, m), 7.23 (2 H, d, J=8.4 Hz), 7.03 (1 H, br s), 7.00 (1 H, br s), 4.62–4.54 (2 H, m), 2.55–2.06 (8 H, m), 2.37 (3 H, s)

Preparation of requisite 4-(2-methylimidazol-1-yl)phenyliodide was as follows;

To a stirred solution of 2-methylimidazole (13.6 g, 165 mmol) in DMF (500 ml) was added sodium hydride (60 % w/w dispersion in mineral oil, 6.60 g, 165 mmol) in portions over 10 min. The resulting white suspension was stirred at room temperature for 30 min, 4-fluoro-1-iodobenzene (33.3 g, 150 mmol) added and the mixture heated at 100 ° C. for 16 h. After the bulk of DMF was removed by evaporation, the resulting residue was partitioned between a mixture of ethyl acetate-toluene (2:1 v/v, 500 ml) and water (250 ml). The organic layer was separated and washed with water (250 ml). Product was extracted with 10 % aqueous HCa (2×200 ml) and the combined aqueous extracts neutralized with 30 % aqueous KOH solution. The resulting suspension was extracted with a mixture of ethyl acetatetoluene (2:1 v/v, 3×250 ml) and the combined organic extracts washed with water (2×250 ml), brine (250 ml), dried (MgSO₄) and concentrated to dryness. The crude product was recrystallized from toluene to afford the titled compound as off-white solids (21.9 g, 51%).

mp: 136–138 ° C.; ¹H NMR (CCDl₃) δ: 7.65–7.61 (2 H. m), 7.32–7.26 (2 H, m), 7.33 (1 H, d, J=1.5 Hz), 6.98 (1 H, d, J=1.5 Hz), 2.83 (3 H, s)

Example 2 endo-3-Aminocarbonyl-exo-3-[3-[4-(2-methylimidazol-1-yl) phenyl]thiophenyl]-8-oxabicyclo [3.2.1]octane To a solution of endo-3-cyano-exo-3-[3-[4-(2-methylimidazol-1-yl)phenyl]thiophenyl]-8-oxabicyclo [3.2.1]octane (190 mg, 0.48 mmol) in tert-butanol (5 ml) were added potassium tert-butoxide (561 mg, 5.0 mmol) and water (90 μl). The mixture was then heated at reflux with stirring overnight. The reaction mixture was cooled and volatiles removed under reduced pressure. To the residue was added a mixture of water (12.5 ml) and brine (12.5 ml) and the suspension extracted with ethyl acetate (25 ml×2). The combined organic layers were washed with a mixture of water (12.5 ml) and brine (12.5 ml) and then with brine (25 ml), dried (MgSO₄) and concentrated to dryness. The crude product was recrystallized from isopropanol to afford 140 mg (70 %) of the titled compound as white solids.

mp: 217–218 ° C.; ¹H-NMR (DMSO-d₆) δ: 7.46–7.31 (8 H, m), 7.28–7.21 (2 H, m), 7.04 (1 H, br s), 6.90 (1 H, d, J=1.5 Hz), 4.35–4.28 (2 H, m), 2.83 (2 H, br d, J=13.6 Hz), 2.28 (3 H, s), 2.00–1.90 (2 H. m), 1.82 (2 H, br d, J=15 13.6 Hz), 1.75–1.62 (2 H, m)

Example 3 exo-3-Cyano-endo-3-[3-[4-(2-methylimidazol-1-yl) phenyl]thiophenyl]-8-oxabicyclo[3.2.1]octane The titled compound was obtained as a colorless liquid according to step C in example 1 using exo-3-cyano-endo-3-(3-iodophenyl)-8-oxabicyclo[3.2.1]octane (2) in place of endo-3-cyano-exo-3-(3-iodophenyl)-8-oxabicyclo[3.2.1]octane (1).

$^1$H NMR (CDCl$_3$) δ: 7.61–7.18 (8 H, m), 7.08–6.92 (2 H, m), 4.59–4.45 (2 H, m), 2.80–2.78 (2 H, m), 2.37 (3 H, s), 2.18–2.15 (2 H, m), 2.00–1.87 (2 H, m), 1.50–1.39 (2H, m)

Example 4 exo-3-Aminocarbonyl-endo -3-[3-[4-(2-methylimidazol- 1-yl)phenyl]thiophenyl]-8-oxabicyclo [3.2.1]octane The titled compound was prepared according to the procedure described for example 2, using exo-3-cyano-endo-3-[3-[4-(2-methylimidazol-1-yl)phenyl]thiophenyl]-8-oxabicyclo[3.2.1]octane in place of endo-3-cyano-exo-3-[3-[4-(2-methylimidazol-1-yl)phenyl]thiophenyl]-8-oxabicyclo[3.2.1]octane.

mp: 181–183 ° C. (ethyl acetate-n-hexane); $^1$H-NMR (CDCl$_3$) δ: 7.67–7.64 (1 H, m), 7.57–7.52 (1 H, m), 7.42–7.32 (4 H, m), 7.23 (2H, d, J=8.4 Hz), 7.03 (1 H, br s), 6.99 (1 H, br s), 5.10 (2 H, br s), 4.50–4.42 (2 H, m), 2.70 (2 H, dd, J=4.4, 14.7 Hz), 2.37 (3 H, s), 2.29 (2 H, d, J=14.7 Hz), 1.79–1.71 (2 H, m), 1.44–1.35 (2 H, m)

In addition, the chemical structure of the compounds prepared in Examples 1–4 are summarized in the following Table.

TABLE

| Example # | Chemical Structure |
|---|---|
| 1 | 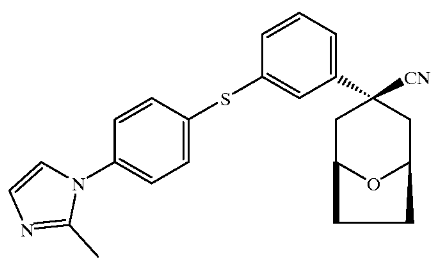 |
| 2 | 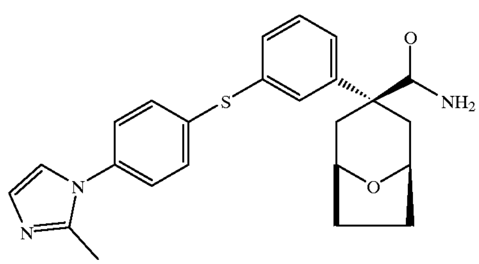 |
| 3 | 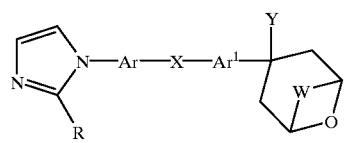 |
| 4 | |

We claim:

1. A compound of formula (I):

I and a pharmaceutically acceptable salt, wherein

Ar is phenylene optionally substituted with halo, hydroxy, cyano, amino, C$_1$–C$_4$ alkyl, C$_1$–C$_4$ alkoxy, C$_1$–C$_4$ alkylthio, C$_1$–C$_4$ halo-substituted alkyl or C$_1$–C$_4$ halo-substituted alkoxy;

X is —A—X$^1$— or X$^1$—A—, wherein A is a direct bond or C$_1$–C$_4$ alkylene, and X$^1$ is oxy, thio, sulfinyl or sulfonyl;

Ar$^1$ is phenylene, pyridylene or thienylene optionally substituted with halo, hydroxy, cyano, nitro, amino, C$_1$–C$_4$ alkyl, C$_1$–C$_4$ alkoxy, C$_1$–C$_4$ alkylthio, C$_1$–C$_4$ halo-substituted alkyl, C$_1$–C$_4$ halo-substituted alkoxy, C$_1$–C$_4$ alkylamino or di(C$_1$–C$_4$)alkylamino;

Y is CN or CONR$^1$R$^2$ wherein R$^1$ and R$^2$ are independently hydrogen or C$_1$–C$_4$ alkyl; and R is hydrogen or C$_1$–C$_6$ alkyl;

W is C$_2$–C$_3$ alkylene, one carbon atom of which may be replaced by an oxygen atom.

2. A compound according to claim 1, wherein Ar is phenylene optionally substituted with halo or C$_1$–C$_4$ alkyl; X is oxy or thio; Ar$^1$ is phenylene optionally substituted with halo or C$_1$–C$_4$ alkyl; Y is CN or CONR$^1$R$^2$ wherein R$^1$ and R$^2$ are independently hydrogen or C$_1$–C$_2$ alkyl; R is C$_1$–C$_3$ alkyl; and W is C$_2$–C$_3$ alkylene.

3. A compound according to claim 1, wherein Ar is 1,4-phenylene optionally substituted with halo or C$_1$–C$_4$ alkyl; Ar$^1$ is 1,3-phenylene optionally substituted with halo or C$_1$–C$_4$ alkyl; and W is C$_2$–C$_3$ alkylene.

4. A compound according to claim 3, wherein X is thio; and W is ethylene.

5. A compound according to claim 4, wherein Ar is 1,4-phenylene; and Ar$^1$ is 1,3-phenylene.

6. A compound according to claim 5, wherein R is methyl; and Y is CN.

7. A compound according to claim 6 selected from:

endo-3-Cyano-exo-3-[3-[4-(2-methylimidazol-1-yl)phenyl]thiophenyl]-8-oxabicyclo[3.2.1]octane or its salts; and exo-3-Cyano-endo-3-[3-[4-(2-methylimidazol-1-yl)phenyl]thiophenyl]-8-oxabicyclo[3.2.1]octane or its salts.

8. A compound according to claim 5, wherein R is methyl; and Y is $CONH_2$.

9. A compound according to claim 8 selected from:

endo-3-Aminocarbonyl-exo-3-[3-[4-(2-methylimidazol-1-yl)phenyl]thiophenyl]-8-oxabicyclo[3.2.1]octane or its salts; and exo-3-Aminocarbonyl-endo-3-[3-[4-(2-methylimidazol-1-yl)phenyl]thiophenyl]-8-oxabicyclo[3.2.1]octane or its salts.

10. A pharmaceutical composition for the treatment of an allergic or inflammatory condition in a mammalian subject, which comprises a therapeutically effective amount of a compound of claim 1 and a pharmaceutically acceptable carrier.

11. A method for treatment of a medical condition for which a 5-lipoxygenase inhibitor is needed, in a mammalian subject, which comprises administering to said subject a therapeutically effective amount of a compound according to claim 1.

* * * * *